(12) United States Patent
Nihalani et al.

(10) Patent No.: US 11,642,235 B2
(45) Date of Patent: May 9, 2023

(54) GASTRIC VEST FOR RESTRICTION OF THE STOMACH TO TREAT OBESITY

(71) Applicant: Reshape Lifesciences, Inc., San Clemente, CA (US)

(72) Inventors: Raj Nihalani, Irvine, CA (US); Reynz Delina, San Clemente, CA (US)

(73) Assignee: ARMISTICE CAPITAL MASTER FUND LTD., New York, NY (US)

( * ) Notice: Subject to any disclaimer, the term of this patent is extended or adjusted under 35 U.S.C. 154(b) by 921 days.

(21) Appl. No.: 16/326,607

(22) PCT Filed: Oct. 4, 2018

(86) PCT No.: PCT/US2018/054434
§ 371 (c)(1),
(2) Date: Feb. 19, 2019

(87) PCT Pub. No.: WO2019/071022
PCT Pub. Date: Apr. 11, 2019

(65) Prior Publication Data
US 2021/0330483 A1     Oct. 28, 2021

Related U.S. Application Data

(60) Provisional application No. 62/568,229, filed on Oct. 4, 2017.

(51) Int. Cl.
    *A61F 5/00*        (2006.01)
(52) U.S. Cl.
    CPC .......... *A61F 5/0063* (2013.01); *A61F 5/0066* (2013.01); *A61F 5/0076* (2013.01)

(58) Field of Classification Search
CPC .... A61F 5/0063; A61F 5/0066; A61F 5/0076; A61F 5/0003; A61F 2/0031;
(Continued)

(56) References Cited

U.S. PATENT DOCUMENTS

| 8,764,624 B2 | 7/2014 | Snow et al. |
| 8,800,842 B2 | 8/2014 | Menzel |

(Continued)

FOREIGN PATENT DOCUMENTS

| CN | 104622531 | 5/2015 |
| WO | WO2008/022360 | 2/2009 |
| WO | WO2010/065654 | 6/2010 |

OTHER PUBLICATIONS

International Search Report and Written Opinion of the International Searching Authority dated May 13, 2019 for Corresponding International Patent Application No. PCT/US2018/054434, filed Oct. 4, 2018.

(Continued)

*Primary Examiner* — Carrie R Dorna
(74) *Attorney, Agent, or Firm* — Snell & Wilmer LLP (57) ABSTRACT

A gastric vest system for treating excessive weight or obesity in mammals. The gastric vest system may include a trapezoidal-shaped vest having a left edge, a right edge, an upper indentation, and a lower indentation, and the trapezoidal-shaped vest is configured to be wrapped around a stomach or a modified stomach of a mammal to cover a lesser curvature and a greater curvature of the stomach or the modified stomach.

19 Claims, 11 Drawing Sheets

(58) Field of Classification Search
CPC ........... A61F 2/0036; A61F 2220/0083; A61L 31/18; A61N 2/0031; A61N 2/0036
See application file for complete search history.

(56) References Cited

U.S. PATENT DOCUMENTS

| | | | |
|---|---|---|---|
| 2005/0002984 A1* | 1/2005 | Byrum | A61F 5/0056 424/423 |
| 2005/0119674 A1* | 6/2005 | Gingras | A61F 5/0003 606/151 |
| 2006/0129027 A1* | 6/2006 | Catona | A61F 5/0066 600/37 |
| 2008/0146869 A1* | 6/2008 | Chow | A61L 31/16 600/37 |
| 2009/0157107 A1 | 6/2009 | Kierath et al. | |
| 2010/0145370 A1 | 6/2010 | Nihalani | |
| 2012/0316387 A1 | 12/2012 | Volker | |
| 2013/0261379 A1* | 10/2013 | Bender | A61F 5/0063 600/37 |
| 2013/0261380 A1 | 10/2013 | Otto et al. | |
| 2013/0331642 A1* | 12/2013 | Schauer | A61F 5/0063 600/37 |
| 2014/0051918 A1 | 2/2014 | Raven et al. | |
| 2014/0257033 A1* | 9/2014 | Frering | A61F 5/0066 425/542 |
| 2016/0166417 A1 | 6/2016 | Nihalani | |

OTHER PUBLICATIONS

Manny Cruz, 2016, Most innovative new product award winners, 2016, pp. 1-5, https://mvemail.constantcontact.com/Most-Innovative-New-Product-Awards-2016.html?soid=1110675265706&aid=bueRqwHvDFI (retrieved on May 13, 2019) See p. 3, paragraph 3; fig. 3.

Anonymous: "Most Innovative New Products Award—2016", Connect, Jan. 1, 2016, pp. 1-5, XP055620271, Retrieved from the Internet: URL:https://mvemail.constantcontact.com/Most-Innovative-New-Product-Awards-2016.html?soid=1110675265706&aid=bueRqwHvDFI, [retrieved on Sep. 10, 2019].

* cited by examiner

GASTRIC VEST FOR RESTRICTION OF THE STOMACH TO TREAT OBESITY

CROSS-REFERENCE TO RELATED APPLICATIONS

The present application claims the benefit of U.S. Provisional Application No. 62/568,229, filed Oct. 4, 2017, the entire contents of which are hereby incorporated by reference.

BACKGROUND

1. Field of the Invention

The invention relates to a method and an apparatus for treating obesity and controlling weight gain in mammals, and more specifically, to a gastric vest placed around a stomach or modified stomach to cause a reduced desire for eating, for treating obesity and for controlling weight gain in mammals.

2. Description of the Related Art

Extreme obesity is a major illness in the United States and other developed countries. More than half of Americans are overweight, while nearly one-third are categorized as obese. Obesity is the accumulation of excess fat on the body, and is defined as having a body mass index (BMI) of greater than 30. Many serious long-term health consequences are associated with obesity, such as, hypertension, diabetes, coronary artery disease, stroke, congestive heart failure, venous disease, multiple orthopedic problems, pulmonary insufficiency, sleep apnea and cancers with markedly decreased life expectancy.

Medical management of obesity including dietary, psychotherapy, medications and behavioral modification techniques have yielded extremely poor results in terms of treating obesity. Several surgical procedures have been tried which have bypassed the absorptive surface of the small intestine or have been aimed at reducing the stomach size by either partition, removal of portions of the stomach or bypass. These procedures have been proven both hazardous to perform in morbidly obese patients and have been fraught with numerous life-threatening postoperative complications. Moreover, such operative procedures are often difficult to reverse.

One procedure for treating morbid obesity is referred to as a "biliopancreatic diversion." Biliopancreatic diversion surgery is a reduction of the stomach volume and a diversion of food from the stomach to the final segment of the small intestine, bypassing the beginning and middle portions of the small intestine to limit the amount of nutrients and calories absorbed by the body. This procedure removes about one half of the stomach, and then connects the stomach to the last 250 cm of the small intestine. Some disadvantages of this surgery include patients suffering from protein malnutrition, anemia, gastric retention, diarrhea, abdominal bloating, and intestinal obstruction.

Another bariatric surgery, "gastric bypass," is a bypass connecting the lower compartment of the stomach to the initial portion of the small intestine. This procedure limits the amount of food that can be ingested at one sitting and reduces absorption of food across the small intestine. In addition to surgical complications, patients may also suffer from acute gastric dilation, anastomotic leak, anemia, and dumping syndrome.

Yet another bariatric surgical procedure is "sleeve gastrectomy," which restricts the volume of the stomach by cutting 70-80% of the stomach using a surgical stapler. In this procedure, surgical staplers are used to cut the stomach to imitate a banana-shape. The stomach remnant is removed from the abdominal cavity. In addition to surgical complications, patients undergoing this procedure may suffer from reflux, life-threatening leaks, or bleeding. The newly formed stomach may expand over time.

Minimally invasive procedures and devices which create a feeling of early satiety had been introduced into the marketplace in an attempt to address some of the issues above. The gastric band is a band which encircles the stomach at the region of the fundus-cardia junction; it is a restrictive procedure similar to stomach stapling. The procedure requires general anesthesia, a pneumoperitoneum, muscle paralysis, and extensive dissection of the stomach at the region of the gastro esophageal junction. The procedure also requires continual adjustment of the band, or restriction of a portion of the device. Although less invasive than other bariatric surgical procedures and potentially reversible, the gastric band does not reduce the volume of the stomach by any great extent and some patients report a feeling of hunger most of the time. Furthermore, once implanted, the gastric band, although it is adjustable by percutaneous means, may require many iterative adjustments before it is optimally positioned. In addition, the port used to adjust the gastric band is left inside the patient's body.

Therefore, there is a need for minimally-invasive procedures and devices that eliminate the above-mentioned drawbacks of conventional methods and devices that are currently being used to treat obesity.

SUMMARY

Embodiments disclosed herein include a gastric vest system for treating excessive weight or obesity in mammals. The gastric vest system may include a trapezoidal-shaped vest having a left edge and a right edge, the trapezoidal-shaped vest configured to be snugly positioned around a stomach or a modified stomach of a mammal so that the left edge is adjacent to the right edge when the trapezoidal-shaped vest is snugly positioned around the stomach or the modified stomach. The gastric vest system may include a plurality of connectors on the trapezoidal-shaped vest. The gastric vest system may include a plurality of tabs on the trapezoidal-shaped vest, each of the plurality of tabs having an opening for insertion of a respective one of the plurality of connectors.

Embodiments disclosed herein include a gastric vest system for treating excessive weight or obesity in mammals. The gastric vest system may include a trapezoidal-shaped vest having a left edge, a right edge, an upper indentation, and a lower indentation, and the trapezoidal-shaped vest is configured to be wrapped around a stomach or a modified stomach of a mammal to cover a lesser curvature and a greater curvature of the stomach or the modified stomach.

Embodiments disclosed herein include a method for treating excessive weight or obesity in mammals. The method may include wrapping a trapezoidal-shaped vest around a stomach or a modified stomach of a mammal. The method may include securing a plurality of connectors on the trapezoidal-shaped vest to a plurality of tabs on the trapezoidal-shaped vest, to secure the trapezoidal-shaped vest around the stomach or the modified stomach.

Embodiments disclosed herein include a gastric vest system for treating excessive weight or obesity in mammals.

The gastric vest system may include a trapezoidal-shaped vest having a top surface, a bottom cutout, a top cutout being larger in surface area than the bottom cutout, a left edge, and a right edge, the vest made of a silicon elastomer material and configured to be snugly positioned around a stomach or a modified stomach of a mammal so that the left edge is adjacent to the right edge when the vest is tightly positioned around the stomach or the modified stomach. The gastric vest system may include a plurality of tabs molded to the vest and being positioned on the top surface of the vest, each tab having a contact portion defining and surrounding an opening. The gastric vest system may include a plurality of flexible connectors molded to the left edge or the right edge of the vest, each flexible connector having a protrusion or a ridge and being able to be inserted through the opening of a respective tab so that the protrusion or the ridge is held in place by the contact portion of the tab in order to secure the vest around the stomach or the modified stomach.

BRIEF DESCRIPTION OF THE DRAWINGS

These and other embodiments of the invention will be discussed with reference to the following exemplary and non-limiting illustrations, in which like elements are numbered similarly, and where.

DETAILED DESCRIPTION

Figure 1:
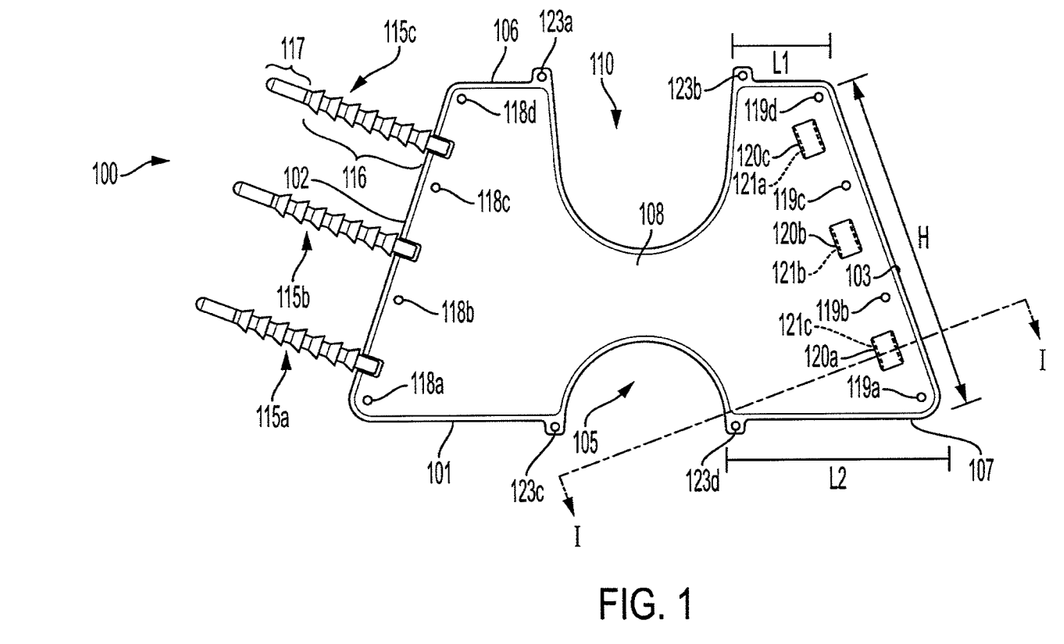
FIG. 1 is a plan view of a gastric vest system including a laid-open trapezoidal-shaped gastric vest, three flexible connectors extending from one side (e.g., left side) of the gastric vest, and three tabs with openings on the other side (e.g., right side) of the gastric vest, according to an embodiment of the invention.
Figure 2:
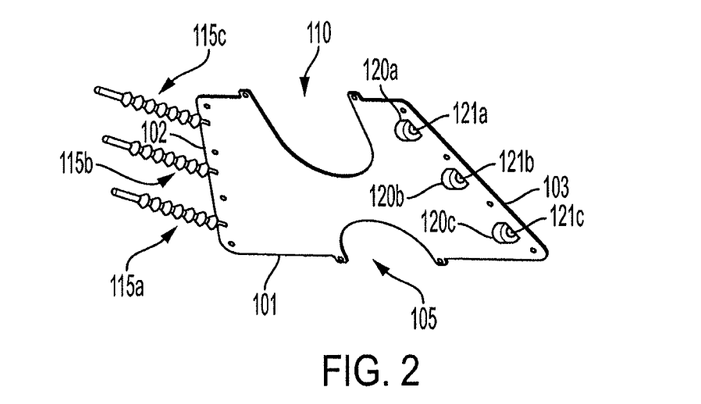
FIG. 2 is a perspective view of the gastric vest system shown in FIG. 1 according to an embodiment of the invention.

FIGS. 1 and 2 are views of a gastric vest system 100 including a laid-open trapezoidal-shaped gastric vest 101 having a left edge 102, a right edge 103, a plurality of flexible connectors 115 (e.g., three flexible connectors 115a-c) extending outward from one edge (e.g., left edge 102) of the gastric vest 101, and a plurality of tabs 120 with openings 121 (visible in FIGS. 2 and 3) (e.g., three tabs 120a-c with openings 121a-c) on one side (e.g., right side) of the gastric vest 101 for insertion and securing to the respective three flexible connectors 115a-c according to an embodiment of the invention. The gastric vest 101 may include a top surface 108. The plurality of flexible connectors 115 and the tabs 120 may be coupled to the top surface 108. The trapezoidal-shaped gastric vest 101 may be configured to be snugly positioned around a stomach or a modified stomach of a mammal so that the left edge 102 is adjacent to the right edge 103 when the vest 101 is snugly positioned around the stomach or the modified stomach.

The gastric vest 101 advantageously and uniquely has a trapezoidal shape to allow for a better (e.g., tighter and more snug) fit around the stomach or the modified stomach of a mammal (e.g., a human). The gastric vest 101 is made out of a silicon elastomer material infused with radiopaque material to allow the gastric vest 101 to be seen under x-ray. This advantageously allows a doctor or a technician to ensure that the gastric vest 101 is properly secured or wrapped around the stomach or the modified stomach of the mammal. The plurality of flexible connectors 115 and the plurality of tabs 120 can be made of the same material as the gastric vest 101, for example, both can be made out of a silicon elastomer material infused with radiopaque material. The gastric vest system 100 can be made from a single mold resulting in a single material that forms the gastric vest 101, the plurality of flexible connectors 115 and the plurality of tabs 120. The plurality of connectors 115 can also be semi-flexible or semi-rigid.

A top edge 106 and a bottom edge 107 may each extend between the left edge 102 and the right edge 103. The top edge 106 may be at a top portion of the gastric vest 101 and the bottom edge 107 may be at a bottom portion of the gastric vest 101. The left edge 102 and the right edge 103 may be angled towards each other, in a direction from the bottom edge 107 to the top edge 106.

Figure 4:
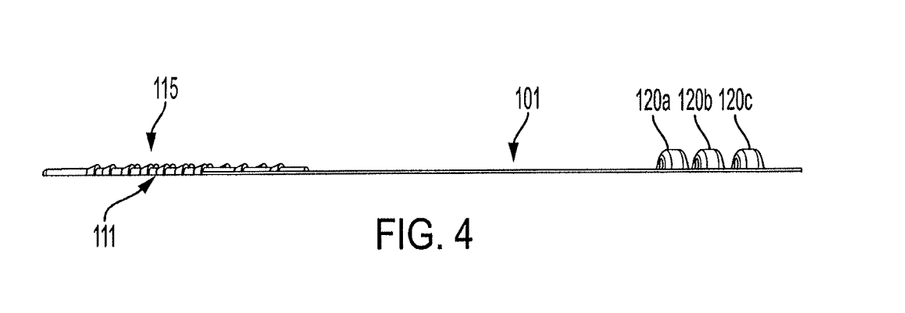
FIG. 4 is a side view of the gastric vest shown in FIG. 1 with the flexible connectors and the tabs being positioned on one side according to an embodiment of the invention.
Figure 5:
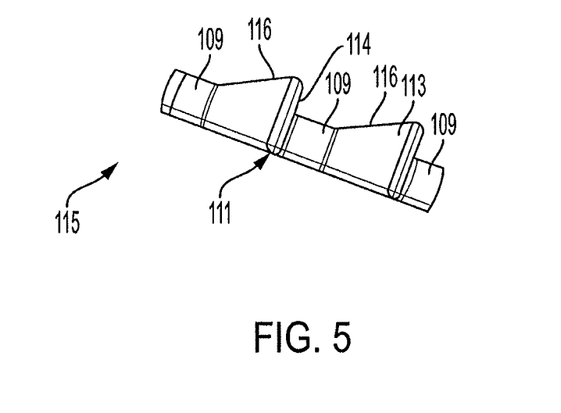
FIG. 5 is a detail view of a portion of a flexible connector shown in FIG. 1 according to an embodiment of the invention.
Figure 6:
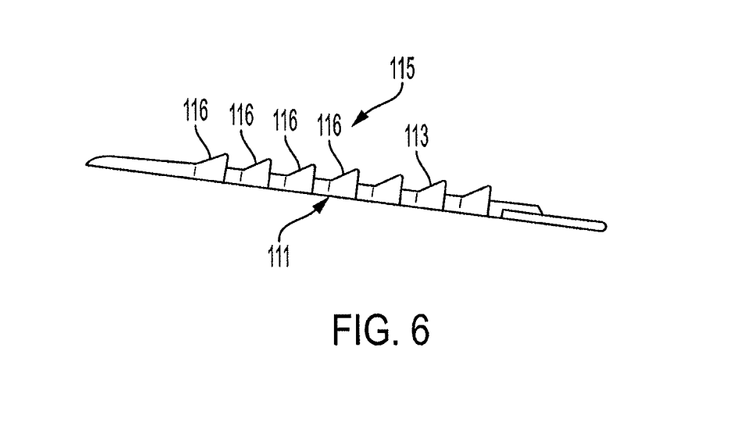
FIG. 6 is a side view of a flexible connector shown in FIG. 1 according to an embodiment of the invention.

Each of the three flexible connectors 115a-c has a plurality of protrusions or ridges 116 (e.g., 7 ridges are shown) formed in the shape of a bucket or a cone and a cylindrical tapered end 117. The flexible connectors 115a-c may each be aligned and positioned to be perpendicular to the edge of the gastric vest 101 as shown in FIG. 1. In one embodiment, the plurality of protrusions or ridges 116 and the cylindrical tapered end 117 are only on one side or cut in half as shown in FIGS. 4-6. This advantageously allows for a lower profile, easier insertion and a more compact design while still maintaining the secure attachment of the flexible connectors 115a-c to the tabs 120a-c. For example, the flat side 111 of the flexible connectors 115 can easily slide along the surface 108 of the gastric vest 101 and into the opening 121 of the tab 120 without snagging on the gastric vest 101 (see e.g. FIG. 4). Thus, the protrusion or ridge 116 may extend only partially around an outer surface 113 of the connector 115 (as marked in FIGS. 5 and 6). The protrusions or ridges 116 may extend in series with each other to form a longitudinal shape for the connector 115, with the tapered end 117 at the end of the connector 115. Referring to FIG. 5, the protrusions or ridges 116 may be connected by connector portions 109 that may have a substantially constant outer surface area between the protrusions or ridges 116. The series of alternating protrusions or ridges 116 and connector portions 109 may form the longitudinal shape for the connector 115.

In one embodiment, the tab 120 has a maximum height of 6.75 millimeters. In one embodiment, the tab 120 may have a different height as desired. In one embodiment, the tabs 120 may be aligned and positioned to be perpendicular to the edge (e.g., right edge 103) of the gastric vest 101 as shown in FIG. 1. This perpendicular alignment and positioning of the flexible connectors 115 and the tabs 120 provide for an easier connection when the gastric vest 101 is covering the stomach or the modified stomach as shown, for example, in FIGS. 9-11.

Referring to FIG. 1, the three flexible connectors 115a-c are formed to be part of, integrated on or to the gastric vest 101. For example, the gastric vest 101, the plurality of protrusions or ridges 116 and the tabs 120a-c are all molded together resulting in one piece of material to provide a stronger hold and prevent the flexible connectors 115a-c and the tabs 120a-c from separating or detaching from the gastric vest 101. When connected, the flexible connectors 115a-c and the tabs 120a-c can be secured together to withstand the intragastric pressure of the stomach or the modified stomach at approximately 1.0 pound per square inch (psi).

In one embodiment, as an example, the top length L1 of the top edge 106 adjacent the right or left edge (103, 102) is 2.5 centimeters (cm), the bottom length L2 of the bottom edge 107 adjacent the right or left edge (103, 102) is 6.1 cm, and the height H or length of the right or left edge (103, 102) is 9.9 cm. Therefore, when the gastric vest 101 covers the stomach or the modified stomach of the mammal, each flexible connector 115a-c is pulled through each respective opening 121a-c to allow the gastric vest 101 to be tightly secured and wrapped around the stomach or the modified stomach of the mammal. In embodiment, the dimensions provided may be varied as desired.

Figure 7:
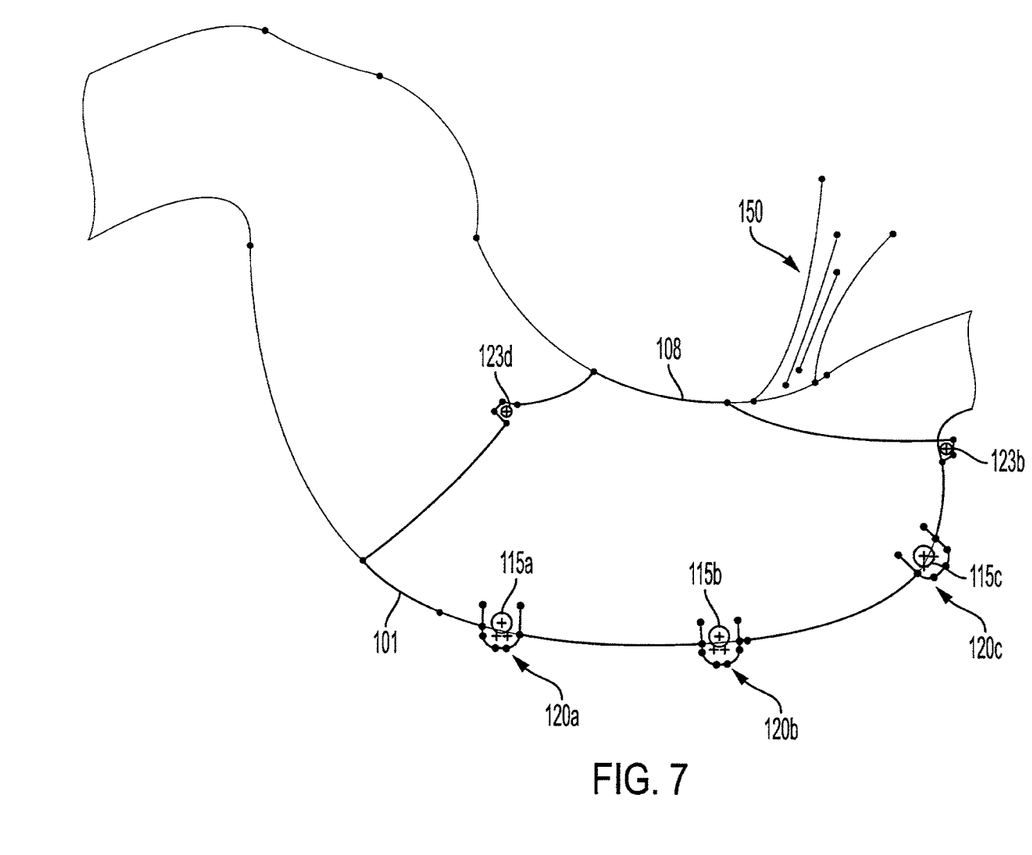
FIG. 7 is a two-dimensional representation of the gastric vest shown in FIG. 1 positioned around a stomach or a modified stomach of a mammal according to an embodiment of the invention.

The gastric vest 101 has a lower indentation 105 and an upper indentation 110. The lower indentation 105 is a bottom cutout of the gastric vest 101 and has the shape of a semi-circle or is U-shaped. Similarly, the upper indentation 110 is a top cutout of the gastric vest 101 and has the shape of a semi-circle or is U-shaped. The cutout of the upper indentation 110 is larger, has a greater opening and a larger surface area and goes further into the gastric vest 101 than the cutout of the lower indentation 105. The larger cutout is to avoid or to go around or otherwise accommodate the gastric arteries 150 as shown in FIG. 7. The indentations 105 and 110 can be any shape such as an ellipse, oval, hourglass, or perforated for a cut-out. For example, each indentation 105 and 110 can be formed or cutout in the shape of a square, a triangle, an oval, a semi-circle, an ellipse, a wave, a curve, or any other shape that creates an indentation. The size of each indentation 105 and 110 can be varied or customized in order to provide an optimal fit around the stomach or the modified stomach. The indentations 105 and 110 do not necessarily have to be the same shape or size as one another.

The lower indentation or cutout may be formed by the bottom edge 107 of the gastric vest 101. The upper indentation or cutout may be formed by the top edge 106 of the gastric vest 101. The bottom portion of the gastric vest 101 may include the lower indentation or cutout, and the top portion of the gastric vest 101 may include the upper indentation or cutout. The lower indentation or cutout may extend in a direction towards the top edge 106 of the gastric vest 101. The upper indentation or cutout may extend in a direction towards the bottom edge 107 of the gastric vest 101. In one embodiment, the lower indentation 105 may be a first indentation and the upper indentation 110 may be a second indentation. The bottom cutout may be a first cutout and the top cutout may be a second cutout.

Figure 3:
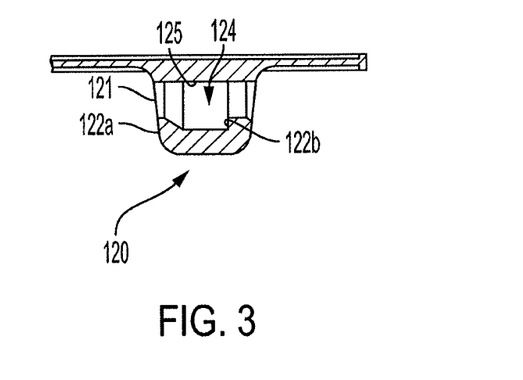
FIG. 3 is a cross-sectional view of a tab along line I-I in FIG. 1 according to an embodiment of the invention.
Figure 8:
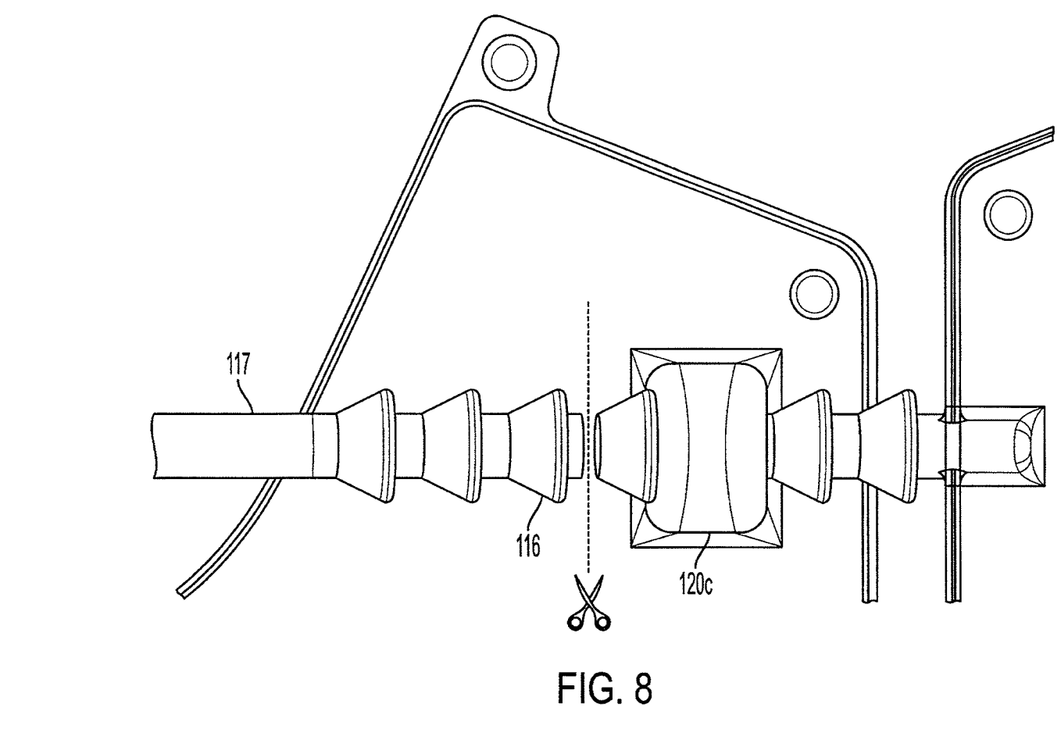
FIG. 8 is an exploded side view of a flexible connector and a tab shown in FIG. 1 according to an embodiment of the invention.

FIG. 3 is a cross-sectional view of a tab 120 of FIG. 1 along line I-I in FIG. 1 according to an embodiment of the invention. The cross-sectional view of the tab 120 may be of any of the tabs 120a, b, c. The cross-sectional area of the opening 121 of the tab 120 is sized to be smaller than the cross-sectional area of the protrusion or ridge 116, which may be semi-circular, round, tapered, square, triangular, trapezoidal or other configurations in shape, so that the tab 120 can securely hold the protrusion or ridge 116 in place in a relatively fixed position. That is, the flat portion 114 (marked in FIG. 5) of the protrusion or ridge 116 extends beyond the opening 121 so that it rests against a contact portion in the form of a surface 122a of the tab 120 so it is difficult to pull the flexible connector 115 back through the opening 121 once inserted through the opening 121. The cross-sectional area of the protrusion or ridge 116 is larger than the cross-sectional area of the opening 121 of the tab 120. A contact portion in the form of a surface 122b may be positioned within a cavity 124 of the tab 120. The surface 122b may securely hold a protrusion or ridge 116 positioned within the cavity 124 in place in a relatively fixed position. In one embodiment, multiple contact portions may be positioned within the cavity 124 to securely hold multiple protrusions or ridges 116 of the connector 115. The tab 120 may include a flat surface 125 that the flat side 111 of the connector 115 may slide along and contact within the cavity 124. The flexible connector 115 can be pulled through the opening 121 by using a medical instrument, such as a laparoscopic grasper, to grab the tapered end 117 of the flexible connector 115 and pull it through the opening 121. Also, as shown in FIG. 8, once the flexible connector 115 is inserted through the opening 121 of the tab 120, the end portion can be cut off. The flexible connector 115 may be cut between two of the plurality of protrusions or ridges 116.

FIG. 4 illustrates a side view of the gastric vest 101. In one embodiment, one or more tabs 120 may be coupled to the gastric vest 101. The configuration of the one or more tabs 120 may be varied as desired. The number of tabs 120 may be varied as desired. In one embodiment, the gastric vest 101 may include other forms of receivers other than tabs for coupling to the connectors 115. In one embodiment, one or more connectors 115 may be coupled to the gastric vest 101. The configuration of the connectors 115 may be varied as desired.

FIG. 5 illustrates a detail view of a protrusion or ridge 116 of the flexible connector 115. The protrusion or ridge 116 may include a flat portion 114. The flat portion 114 may be at a trailing edge of each protrusion or ridge 116, and each protrusion or ridge may taper outward from its leading edge to its trailing edge. The flat portion 114 may be adjacent a connector portion 109. Each flexible connector 115 may include one or more protrusions or ridges 116.

FIG. 6 illustrates a side view of a flexible connector 115.

Figure 9:
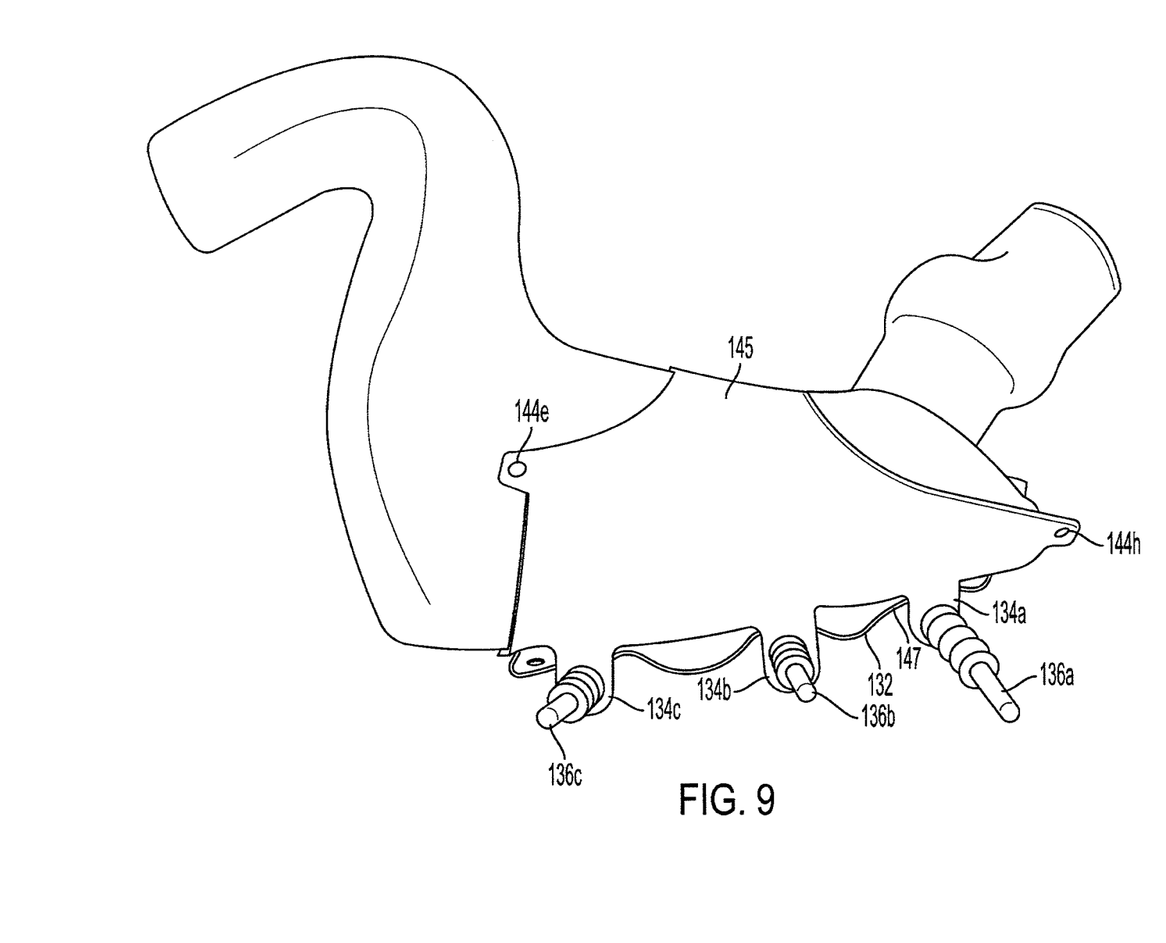
FIG. 9 is a side view of a gastric vest placed in position around a stomach or a modified stomach according to an embodiment of the invention.
Figure 10:
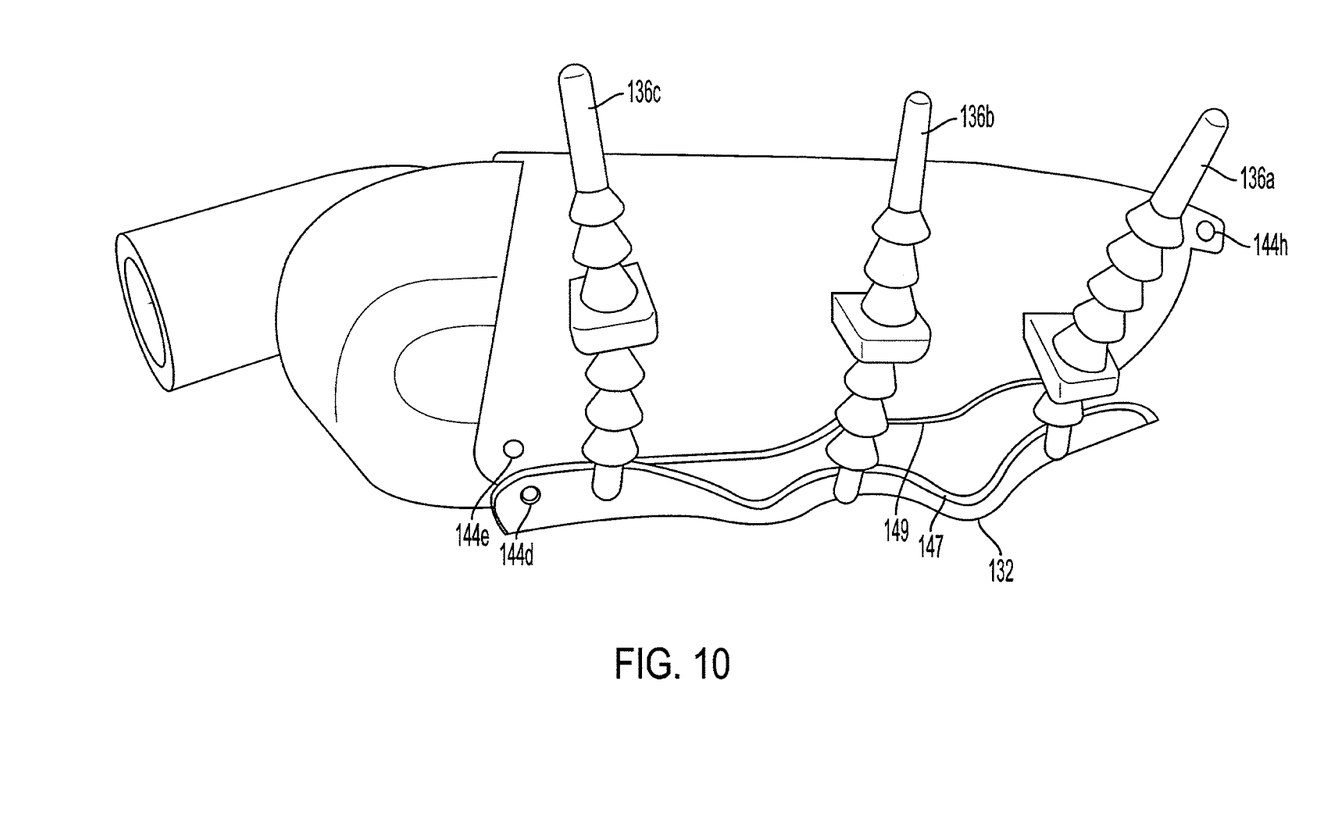
FIG. 10 is a side view of the gastric vest shown in FIG. 9 placed in position around a stomach or a modified stomach according to an embodiment of the invention.
Figure 11:
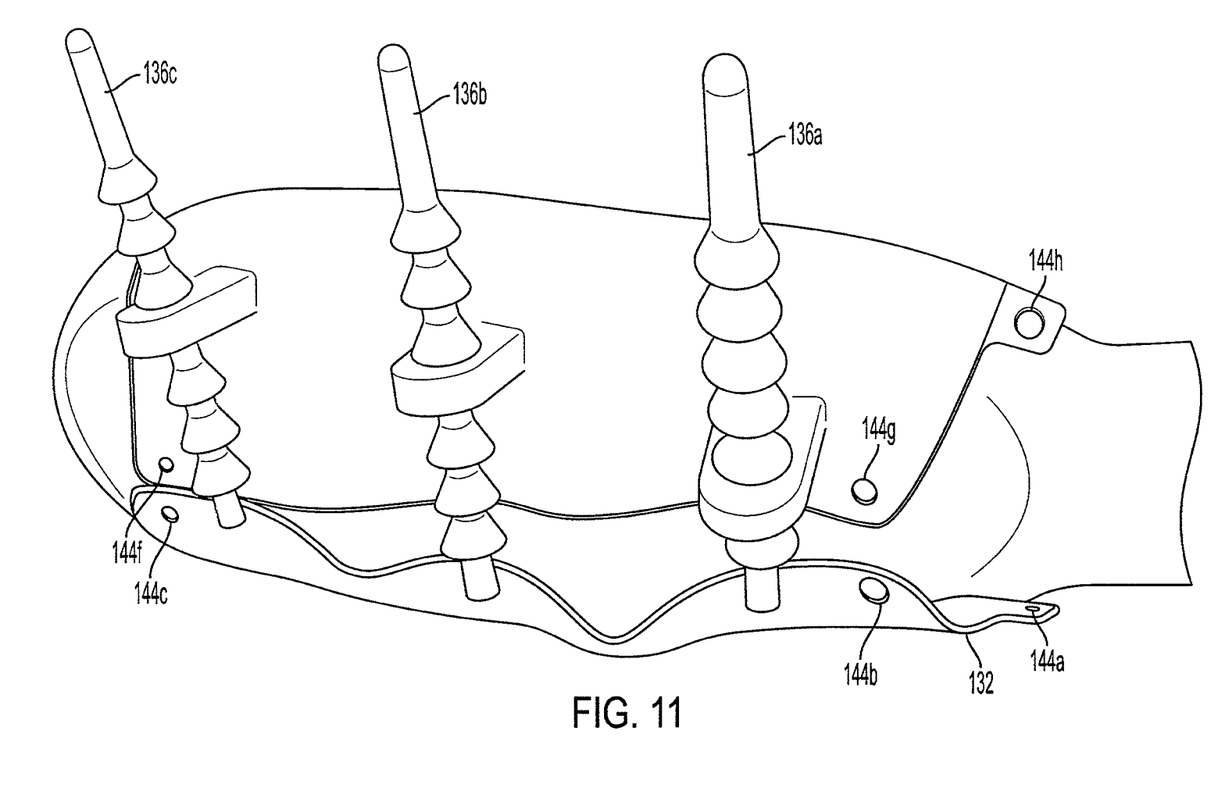
FIG. 11 is a side view of the gastric vest shown in FIG. 9 placed in position around a stomach or a modified stomach according to an embodiment of the invention.

FIGS. 9-11 are various views of a gastric vest 132 placed in position around a stomach or a modified stomach according to an embodiment of the invention. The gastric vest 132 may be used and configured similarly as the gastric vest 101, however, the shape of the connectors may be different than shown in regard to the gastric vest 101. The connectors 136 shown in FIGS. 9-11 may include protrusions or ridges that extend entirely around an outer surface of the respective connectors 136*a-c*.

The left edge 147 of the gastric vest is positioned adjacent to the right edge 149 of the gastric vest in this configuration. Referring to FIGS. 7 and 9-11, when the gastric vest 101, 132 is placed around the stomach or the modified stomach, the gastric vest 101, 132 is formed in a conical tapered shape. This advantageously allows for a better fit around the stomach or the modified stomach. The trapezoidal shape of the gastric vest 101, 132 produces the conical tapered shape when wrapped around the stomach or modified stomach. As shown in FIG. 9, the part of the stomach shown in FIG. 9 distal the gastric vest edges is the lesser curvature of the stomach and the part of the stomach shown in FIG. 9 proximal the gastric vest edges is the greater curvature of the stomach. The gastric vest 132 is shown covering both the lesser curvature and the greater curvature of the stomach or modified stomach.

The gastric vest 101, 132 tapers outward or gets wider and covers more area as it travels from the gastroesophageal (GE) junction of the stomach or the modified stomach to the incisura angularis of the stomach or the modified stomach. This shape is similar to a funnel. That is, the smaller circumference is at the upper portion of the stomach and the larger circumference is at the mid-to-lower portion of the stomach.

Referring back to FIG. 1, the gastric vest 101 also includes a plurality of suture holes 118*a-d* that can be used to connect to corresponding plurality of suture holes 119*a-d* to provide for additional attachment of the gastric vest 101. Covering the upper portion (i.e., the fundus) and the middle portion of the stomach or the modified stomach with the gastric vest 101 aids in satiety (i.e., resulting in the mammal feeling full) and helping the mammal achieve weight loss. The gastric vest 101 is used to completely cover the gastroesophageal junction of the stomach or the modified stomach all the way to the incisura angularis of the stomach or the modified stomach. In one embodiment, the gastric vest 101 does not cover the pylorus since the pylorus does not add much to increase satiety. The suture holes 118*a-d*, 119*a-d* may also be utilized to secure the gastric vest 101 to the stomach or the modified stomach. Sutures may be placed through the suture holes 118*a-d*, 119*a-d* to secure the gastric vest 101 to the stomach or the modified stomach. The gastric vest 101 may also include suture holes 123*a-d* that may be utilized to secure the gastric vest 101 to the stomach or the modified stomach. Sutures may be placed through the suture holes 123*a-d* to secure the gastric vest 101 to the stomach or the modified stomach. In one embodiment, sutures may be placed through the suture holes 123*a, b* to suture the holes 123*a, b* together.

A method for treating excess weight or obesity in mammals may include a method of implanting the gastric vest 101, 132 around a stomach or modified stomach of a mammal. The steps may include accessing the stomach or modified stomach of the mammal, which may be a medical patient. The stomach or modified stomach may be accessed through a variety of methods, which may include laparoscopic entry of the patient's body. The stomach or modified stomach may then be gripped with a medical instrument, such as a laparoscopic grasper, and may be folded. The stomach or modified stomach may be folded upon itself to reduce the interior volume of the stomach or modified stomach. The stomach or modified stomach may then be sutured to itself to secure the stomach or modified stomach in the folded configuration. After the stomach or modified stomach is in the folded configuration, the gastric vest 101, 132 may be inserted into the patient's body. The gastric vest 101, 132 may be inserted in an unexpanded configuration, in which the gastric vest 101, 132 has a smaller total size than when extended around the stomach or modified stomach. For example, the gastric vest 101, 132 may be inserted into the patient's body in a folded or rolled configuration. The gastric vest 101, 132 may then be extended around the folded stomach or folded modified stomach. The connectors 115, 136 may then be gripped with a medical instrument, such as a laparoscopic grasper, to insert the connectors 115, 132 through the openings of the respective tabs 120, 134.

The fit of the gastric vest 101, 132 may be adjusted by determining the number of protrusions or ridges 116, 138 that pass through the opening 121, 140 of the respective tab 120, 134. The gastric vest 101, 132 in this configuration may have an appearance as shown in FIGS. 9-11. Upon determining the appropriate fit of the gastric vest 101 upon the folded stomach or modified stomach, the user (such as a surgeon or other medical professional) may suture the gastric vest 101, 132 to the folded stomach or modified stomach, for example, via the suture holes 118*a-d*, 119*a-d*, 123*a-d*, 144*a-h*. The user may then cut off or otherwise remove an excess portion of the connector 115, 136 that extends through the opening 121, 140 of the respective tab 120, 134, for example, as shown in FIG. 8. The gastric vest 101, 132 may be utilized to support the stomach or modified stomach and to prevent the stomach or modified stomach from further expansion while the gastric vest 101, 132 is placed on the stomach or modified stomach. The method disclosed herein may be varied in other embodiments as desired. Steps may be excluded, modified, added to, or otherwise varied as desired.

Figure 12:
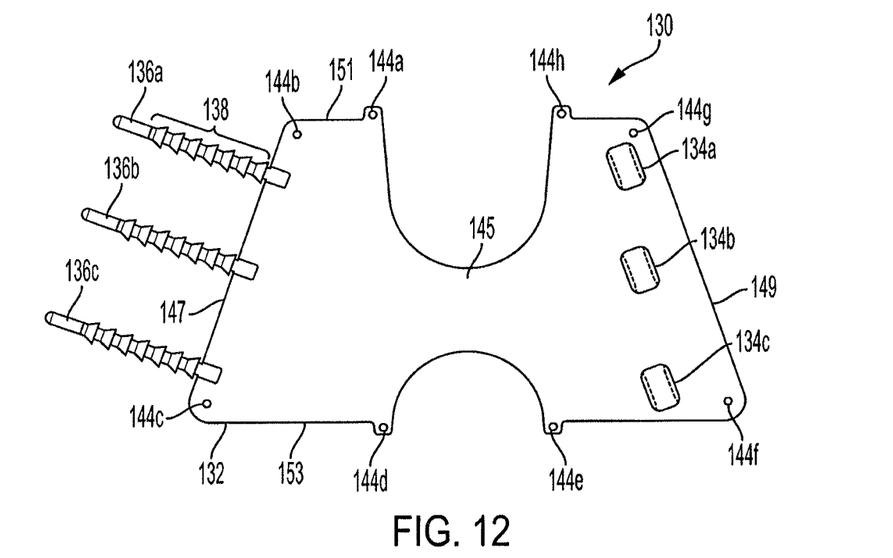
FIG. 12 is a plan view of a gastric vest system according to an embodiment of the invention.

FIG. 12 shows a plan view of a gastric vest system 130 including the gastric vest 132, the plurality of tabs 134*a-c*, and the plurality of connectors 136*a-c*. The gastric vest 132 is configured similarly as the gastric vest 101 shown in FIG. 1. However, the connectors 136*a-c* in this embodiment include protrusions or ridges 138 that extend entirely around an outer surface of the respective connectors 136*a-c*. The gastric vest 132 may include a left edge 147, a right edge 149, a top edge 151, a bottom edge 153, and a top surface 145. The top edge 151 may form an upper indentation or cutout, and the bottom edge 153 may form a lower indentation or cutout.

Figure 13:
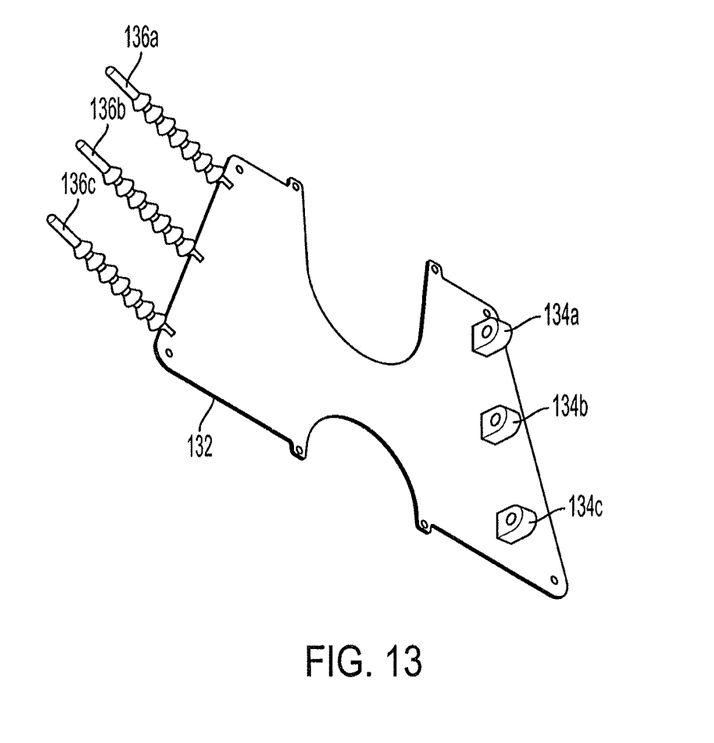
FIG. 13 is a perspective view of the gastric vest system shown in FIG. 12 according to an embodiment of the invention.
Figure 14:
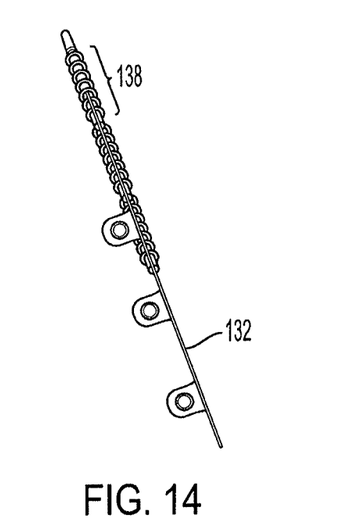
FIG. 14 is a side view of the gastric vest shown in FIG. 12 according to an embodiment of the invention.

FIG. 13 illustrates a perspective view of the gastric vest 132. FIG. 14 illustrates a side view of the gastric vest 132. The protrusions or ridges 138 are visible extending entirely around the outer surface of the respective connector.

Figure 15:
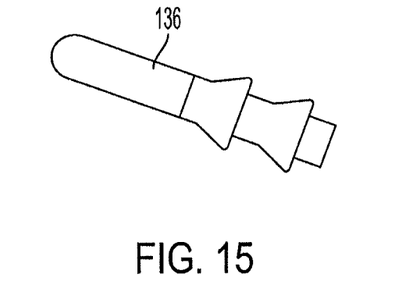
FIG. 15 is a detail view of a portion of a flexible connector shown in FIG. 12 according to an embodiment of the invention.
Figure 16:
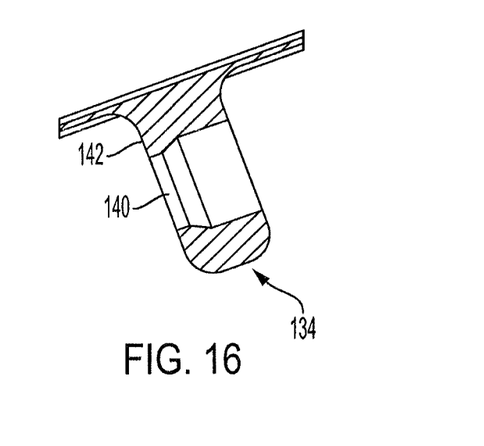
FIG. 16 is a cross-sectional view of a tab of FIG. 12 according to an embodiment of the invention.

FIG. 15 illustrates a side view of a portion of the connector 136. FIG. 16 illustrates a cross section view of one of the tabs 134. The tab 134 may include an opening 140 and a contact portion in the form of a surface 142 for the protrusions or ridges 138 to contact, similar to the surface 122*a* in FIG. 3.

Figure 17:
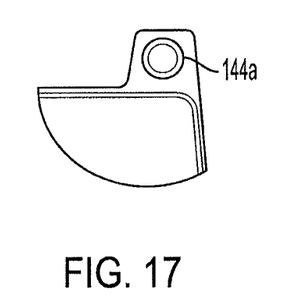
FIG. 17 is a detail view of a suture hole shown in FIG. 12 according to an embodiment of the invention.

FIG. 17 illustrates a detail view of a suture hole 144*a*, which may be configured similarly as the suture hole 123*a* shown in FIG. 1. The suture holes 144*a-h* (marked in FIG.

12) may be utilized to secure the gastric vest 132 to the stomach or modified stomach, or may be utilized to secure the suture holes 144a-h to each other, in a similar manner as described regarding suture holes 118a-d, 119a-d, 123a-d.

Figure 18:
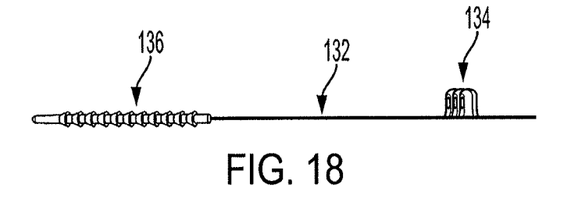
FIG. 18 is a side view of the gastric vest shown in FIG. 12 according to an embodiment of the invention.
Figure 19:
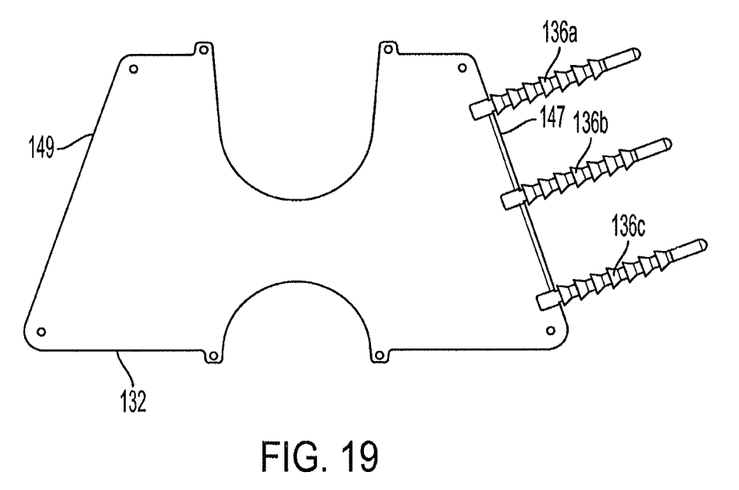
FIG. 19 is a plan view of the gastric vest shown in FIG. 12 according to an embodiment of the invention.

FIG. 18 illustrates a side view of the gastric vest 132. FIG. 19 illustrates a plan view of the gastric vest 132 on an opposite side of the gastric vest 132 than shown in FIG. 12.

While the principles of the disclosure have been illustrated in relation to the exemplary embodiments shown herein, the principles of the disclosure are not limited thereto and include any modification, variation or permutation thereof.

What is claimed is:

1. A gastric vest system for treating excessive weight or obesity in mammals, comprising:
   a trapezoidal-shaped vest having a first edge and a second edge, the trapezoidal-shaped vest configured to be snugly positioned around a stomach or a modified stomach of a mammal so that the first edge is adjacent to the second edge when the trapezoidal-shaped vest is snugly positioned around the stomach or the modified stomach;
   a plurality of tabs positioned spaced along and inset from the first edge and extending upward from a surface of the trapezoidal-shaped vest, each of the plurality of tabs having a closed lower surface, a contact portion and an opening between the closed lower surface and the contact portion; and
   a plurality of connectors extending outward from and spaced along the second edge of the trapezoidal-shaped vest opposite the first edge, each of the plurality of connectors having a plurality of protrusions for securing to one of the plurality of tabs and configured to be inserted through the opening of the one of plurality of tabs;
   wherein each of the plurality of connectors is configured to be adjusted between a plurality of configurations when snugly positioned by passing a protrusion of the plurality of protrusions through the opening of one of the plurality of tabs and secured against the respective contact portion of the one of the plurality of tabs.

2. The gastric vest system of claim 1, wherein the trapezoidal-shaped vest is made of a silicon elastomer material infused with radiopaque material to allow the trapezoidal-shaped vest to be seen under x-ray.

3. The gastric vest system of claim 1, wherein the trapezoidal-shaped vest includes a top cutout and a bottom cutout.

4. The gastric vest system of claim 3, wherein the top cutout is larger in surface area than the bottom cutout.

5. The gastric vest system of claim 3, wherein the top cutout is configured to accommodate gastric arteries.

6. The gastric vest system of claim 3, wherein the top cutout has a shape of a semi-circle or a U-shape.

7. The gastric vest system of claim 1, wherein each of the plurality of connectors extends outward from the first edge or the second edge of the trapezoidal-shaped vest.

8. The gastric vest system of claim 1, wherein each protrusion of the plurality of protrusions has a flat portion for resting against the contact portion.

9. The gastric vest system of claim 1, wherein a cross-sectional area of each protrusion of the plurality of protrusions is larger than a cross-sectional area of a respective one of the plurality of openings.

10. The gastric vest system of claim 1, wherein each of the plurality of connectors has a flat side.

11. The gastric vest system of claim 1, wherein the trapezoidal-shaped vest is configured to cover a lesser curvature and a greater curvature of the stomach or the modified stomach when the trapezoidal-shaped vest is snugly positioned around the stomach or the modified stomach.

12. The gastric vest system of claim 1, wherein the plurality of tabs are aligned and positioned perpendicular to the first edge.

13. The gastric vest system of claim 1, wherein each of the plurality of protrusions comprises a bucket shape or a cone shape.

14. The gastric vest system of claim 1, wherein each of the plurality of connectors terminates in a cylindrical tapered end.

15. The gastric vest system of claim 1, wherein the plurality of connectors, the plurality of tabs, and the trapezoidal-shaped vest are formed from a single molded material.

16. A method for treating excessive weight or obesity in mammals, comprising:
   wrapping a trapezoidal-shaped vest around a stomach or a modified stomach of a mammal, the trapezoidal-shaped vest comprising a first edge and a second edge, a plurality of tabs positioned spaced along and inset from the first edge and extending upward from a surface of the trapezoidal-shaped vest, each of the plurality of tabs having a closed lower surface, a contact portion and an opening between the closed lower surface and the contact portion, and a plurality of connectors extending outward from and spaced along the second edge of the trapezoidal-shaped vest opposite the first edge, each of the plurality of connectors having a plurality of protrusions for securing to one of the plurality of tabs and configured to be inserted through the opening of the one of plurality of tabs; and
   securing the plurality of connectors to the plurality of tabs so that the first edge is adjacent to the second edge when the trapezoidal-shaped vest is snugly positioned around the stomach or the modified stomach.

17. The method of claim 16, further comprising:
   adjusting the plurality of connectors between a plurality of configurations when snugly positioned by passing the one of the plurality of protrusions through the opening of the one of the plurality of tabs and being secured against the contact portion of the one of the plurality of tabs.

18. The method of claim 16, wherein the trapezoidal-shaped vest comprises an upper indentation, and the upper indentation goes around gastric arteries when the trapezoidal-shaped vest is wrapped around the stomach or the modified stomach.

19. The method of claim 16, wherein the trapezoidal-shaped vest covers a lesser curvature and a greater curvature of the stomach or the modified stomach when the trapezoidal-shaped vest is wrapped around the stomach or the modified stomach.

* * * * *